United States Patent [19]

Strecker

[11] Patent Number: 4,466,113

[45] Date of Patent: Aug. 14, 1984

[54] X-RAY EXAMINATION DEVICE HAVING A HIGH LOCAL RESOLUTION

[75] Inventor: Helmut Strecker, Hamburg, Fed. Rep. of Germany

[73] Assignee: U.S. Philips Corporation, New York, N.Y.

[21] Appl. No.: 345,183

[22] Filed: Feb. 2, 1982

[30] Foreign Application Priority Data

Feb. 6, 1981 [DE] Fed. Rep. of Germany ....... 3104052

[51] Int. Cl.$^3$ ............................................. G03B 41/16
[52] U.S. Cl. ..................................... 378/146; 378/149
[58] Field of Search ................................ 378/146, 149

[56] References Cited

U.S. PATENT DOCUMENTS 3,944,833  3/1976  Hounsfield ........................... 378/19
4,160,167  7/1979  Weiss .................................... 378/19
4,366,574  12/1982  Hill ..................................... 378/146

Primary Examiner—Craig E. Church
Attorney, Agent, or Firm—Paul R. Miller

[57] ABSTRACT

In an X-ray examination device which comprises an X-ray source for irradiating a body and a detector device, a displaceable diaphragm device defines an angle of aperture which is substantially smaller, due to the selection of the dimension of the apertures, than the measuring angle defined by the associated radiation detector and the X-ray source. By displacement of the aperture with respect to the object to be measured during the measurement over a distance which covers the measuring angle, a high-resolution shadow image can be formed. The entire object is then contiguously irradiated.

17 Claims, 1 Drawing Figure

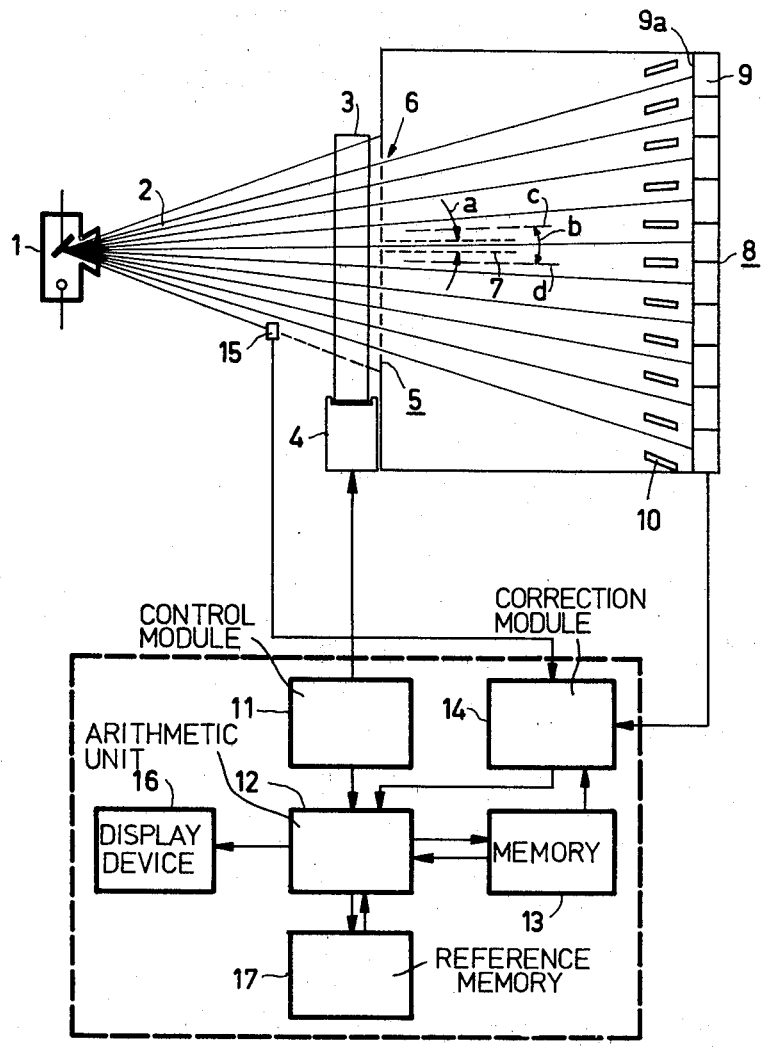

X-RAY EXAMINATION DEVICE HAVING A HIGH LOCAL RESOLUTION

The invention relates to an X-ray examination device, comprising an X-ray source for irradiating an object, a detector device with at least one radiation detector and a diaphragm device which is displaceable with respect to the object with the diaphragm device comprising for each radiation detector an aperture which transmits a scanning radiation beam having an angle of aperture which is smaller, measured in the displacement direction, than the angle of aperture defined by the associated radiation detector and the X-ray source.

A device of this kind is already known from European Pat. No. 000 15 23. Therein, a computer tomography apparatus is described in which a body to be examined is irradiated by means of a fan-shaped radiation beam. In order to enable irradiation of the body with a higher spatial resolution, it is possible to arrange in the beam path a diaphragm device whose apertures are proportioned in accordance with the desired resolution and which can be positioned with respect to the detector by a translatory movement. The body is irradiated in a series of positions of the radiation source and the detector device with respect to the body along beam paths which do not directly adjoin but wherebetween each time body zones which are not irradiated are present.

It is the object of the invention to provide an X-ray examination device whereby a substantially contiguous irradiation image of an object can be obtained with a high local resolution.

To this end, an X-ray examination apparatus of the kind set forth is characterized in that during a measurement a displacement mechanism enables a displacement between the object and the diaphragm device over a distance which covers, measured transversely of the radiation beam, at least the angle of aperture defined by the radiation source and an effective detector entrance face.

It is thus achieved that when the object is irradiated with a cone of fan-shaped (primary) radiation beam which extends mainly in one direction with respect thereto, the object to be examined is scanned substantially without interruptions by means of the scanning beams, i.e. the absorption along the beam paths extending through the apertures can be measured so that a shadow image of the object can be obtained.

When an object is to be scanned with a high local resolution, apertures can be reduced so that the angles of aperture of the scanning radiation beams defined thereby are substantially smaller than the angles of aperture defined by the detector entrance faces.

The absorption values measured by each detector in each position of the diaphragm device with respect to the body are stored in an electronic memory. Subsequently, the absorption values are applied, taking into account the position of the diaphragm device with respect to the body, by means of a computer, to a display unit on which the projection image of the body can be displayed.

The detector device of a preferred embodiment in accordance with the invention consists of a two-dimensional field of radiation detector with the displacement device enabling translatory movements in two mutually transverse directions. In this case the relative displacement between body and diaphragm device thus takes place in two mutually transverse directions, for example, in a meander-like manner. An examination device thus formed offers electronic data sufficiently fast for automation of the serial examination of objects by means of shadow images.

The sole FIGURE shows an embodiment of an examination device in accordance with the invention. For the radiation source 1 use is made of an X-ray tube which emits a spatially diverging (primary) radiation beam 2. The radiation beam 2 penetrates an object 3 to be examined, for example, a workpiece to be examined for material defects which is arranged on a displacement device 4. Directly behind the body 3 there is arranged a diaphragm device 5 which is constructed as a diaphragm plate and which comprises a large number of equally large apertures 6.

So-called scanning radiation beams 7 pass through the apertures 6 to be detected by a two-dimentional detector 8 which is arranged behind the diaphragm device 5 and which consists of seperate radiation detectors 9 which are arranged in a plane parallel to the diaphragm plate. A radiation detector 9 is associated with each aperture 6. The apertures 6 as well as the radiation detectors 9 are arranged in their respective planes in columns and rows of a matrix. The size of the apertures 6 is chosen so that for one direction the angles of aperture a of the scanning radiation beams 7 are substantially smaller than half the measuring angle b of the radiation detectors 9 associated with the scanning radiation beams 7. A measuring angle then forms the angle between two legs c and d of a triangle which originate from the focus of the radiation source 1 with the base of the triangle being the dimension of a radiation detector 9 in the displacement direction.

The diaphragm device 5 consists of, for example, a lead foil having apertures and which is arranged on a radiation-transmitting supporting plate. The supporting plate and lead foil are sealed by means of a thin aluminium layer. The apertures 6 in a special embodiment have, for example, a square shape and are dimensioned $0.1 \times 0.1$ m$^2$, the distance between two apertures 6 being a multiple of their dimension. However, the diaphragm apertures may alternatively have another shape, for example, a rectangular or a circular shape.

At a distance of one meter from the diaphragm device 5 there are situated the detectors 9 which are arranged in accordance with the pattern of the apertures 6 and which each time have a square, radiation-sensitive entrance face 9a of $1 \times 1$ cm$^2$. The detectors 9 are arranged so that they are struck in the center by the X-ray 7 passing through the apertures 6. For shielding against scatter radiation produced in the body and the diaphragm device 5, a scatter shield 10 is arranged very close to and in front of the detector device 8.

In order to enable a contiguous projection image (Shadow image) to be made of the body 3, the body is displaced in the radiation beam 2, parallel to the diaphragm device 5; this is realized by means of the displacement device 4. Thus, the apertures 6 successively image different zones of the body 3 on the corresponding detectors 9 by way of the scanning radiation beams 7, and the absorption along these radiation beams is measured. The movement of the body 3 in the radiation beam 2 offers the advantage that the recording geometry of the examination device does not change and that, for example, radiation inhomogeneities which are constant in time and which are to be taken into account for the formation of the projection image by means of the output signals of the radiation detectors 9, have to be determined only once.

The body 3 is displaced by amounts which correspond to the dimension of the apertures 6 in the direction of displacement. In the case of square apertures 6 arranged in the form of a matrix, the displacement, for example, in the row and the column direction can each time be performed over the length of one aperture 6 when the sides extend parallel or perpendicularly to the rows or columns. The displacement can then be performed in a meander-like manner.

The displacement device 4 is controlled by means of a control module 11 which suitably activates the displacement device 4 for a preselected displacement of the body. The control signals are at the same time applied to an arithmetic unit 12 which calculates the coordinates of the body zones to be scanned after each displacement, or of the scanning radiation beams, and which takes over the assignment of the corresponding measuring data (absorption values) to the coordinates. Subsequently, the measurement data and the coordinates are stored in a memory 13. The measurement data can be corrected in advance in a correction module 14. This correction may be performed as regards radiation inhomogeneities which are constant in time (for example, a decrease of the radiation density at the edges of the radiation cone) as well as for the compensation of the fluctuations in time of the radiation intensity. For the latter case, a reference detector 15 whose output signals are applied to the correction module 14 is arranged in the radiation beam 2. For the testing of contrast-less objects for small defects which become apparent as contrast, the reference detector 15 can be dispensed. Assuming that only few objects occur in an image detail, the sum of all measurement values then represents, if the number of detectors is sufficiently large, a quantity which is essentially dependent only on the fluctuation in time of the radiation density and which is used for the correction.

For the formation of a projection image of the body 3 which is true-to-scale, the measurement data stored in the image memory 13 are applied, via the arithmetic unit 12, to a display device 16 (for example, a monitor or a hard copy apparatus) in which they are combined, taking into account the position coordinates of the relevant scanning radiation beams. The measurement data, however, can also be compared with corresponding data of a reference body which are stored in a reference memory 17 or be processed in another manner. The differences between the reference body and the body 3 actually examined can then be reproduced, for example, on the display apparatus 16.

Evidently, for the formation of the projection image of a body it is alternatively possible to displace the radiation source 1 as well as the diaphragm and detector arrangement 8 relative to the stationary body 3. In that case the displacement device 4 is to be mechanically coupled, for example, to a common support (not shown) for the elements 1, 5 and 8. Similarly, only the diaphragm device 5 can be displaced relative to the stationary body 3 and the stationary elements 1 and 8, be it only so far that the radiation beams formed by the diaphragm device 5 cannot be incident on the edges of the radiation detectors 9.

What is claimed is:

1. An X-ray examination device comprising an object to be examined,
   radiation source means for irradiating said object,
   detector means having a plurality of radiation detectors for detecting radiation from said source means passing through said object,
   diaphragm means having a plurality of apertures corresponding to said plurality of radiation detectors for transmitting a scanning radiation beam from said object to said radiation detectors, said apertures being equally sized to pass said radiation beam with an angle of aperture a smaller than the angle of aperture b defined by said radiation source means and one radiation detector,
   displacement means for providing a displacement transverse to said radiation beam between said object and said diaphragm means over a distance covering at least said angle of aperture b,
   scatter radiation grid means between said diaphragm means and said detector means for shielding said radiation detectors from scattered radiation, and
   control means connected between said displacement means and said detector means for controlling movement of said displacement means and for providing a display of said object.

2. An X-ray device according to claim 1, wherein said detector means includes a two dimensional field of said radiation detectors, and wherein said displacement means provides translatory movement in two mutually transverse directions.

3. An X-ray device according to claim 2, wherein said diaphragm means is a plate-like structure arranged between said detector means and said object and in the direct vicinity of said object.

4. An X-ray device according to claim 3, wherein said radiation source means, said diaphragm means, and said detector means are positioned to be stationary with respect to one another, and wherein said displacement means provides relative displacement therebetween and said object.

5. An X-ray device according to claim 3, wherein only said diaphragm means is displaceable.

6. An X-ray device according to claim 3, wherein a reference radiation detector is arranged between said radiation source means and said object, said radiation detector also being connected to said control means to correct fluctuations in time of radiation intensity.

7. An X-ray device according to claim 2, wherein said radiation source means, said diaphragm means, and said detector means are positioned to be stationary with respect to one another, and wherein said displacement means provides relative displacement therebetween and said object.

8. An X-ray device according to claim 2, wherein only said diaphragm means is displaceable.

9. An X-ray device according to claim 2, wherein a reference radiation detector is arranged between said radiation source means and said object, said radiation detector also being connected to said control means to correct fluctuations in time of radiation intensity.

10. An X-ray device according to claim 2, wherein said apertures have one of a square or a circular shape.

11. An X-ray device according to claim 1, wherein said diaphragm means is a plate-like structure arranged between said detector means and said object and in the direct vicinity of said object.

12. An X-ray device according to claim 1, wherein said radiation source means, said diaphragm means, and said detector means are positioned to be stationary with respect to one another, and wherein said displacement means provides relative displacement therebetween and said object.

13. An X-ray device according to claim 1, wherein only said diaphragm means is displaceable.

14. An X-ray device according to claim 1, wherein a reference radiation detector is arranged between said radiation source means and said object, said radiation detector also being connected to said control means to correct fluctuations in time of radiation intensity.

15. An X-ray device according to claim 1, wherein said apertures have one of a square or a circular shape.

16. An X-ray device according to claim 1, wherein said control means includes a control module circuit for activating said displacement means for a preselected displacement, arithmetic means for calculating coordinates of zones of said object to be scanned after displacement, correction circuit for correcting measurement data, memory circuit for storing said corrected measurement data and said coordinates, and display means for displaying an image of said object.

17. An X-ray device according to claim 16, wherein said control means further includes a reference memory means for storing reference values.

* * * * *